United States Patent [19]

Herd et al.

[11] Patent Number: 5,091,515
[45] Date of Patent: Feb. 25, 1992

[54] PROCESS FOR THE PREPARATION OF SUBSTITUTED 2,4-DIAMINO-6-FLUORO-S-TRIAZINES

[75] Inventors: Karl J. Herd, Odenthal; Hans-Georg Frosch; Hermann Henk, both of Cologne; Wolfgang Müllers, Bergisch-Gladbach; Frank-Michael Stöhr, Odenthal, all of Fed. Rep. of Germany

[73] Assignee: Bayer Aktiengesellschaft, Leverkusen, Fed. Rep. of Germany

[21] Appl. No.: 518,685

[22] Filed: May 3, 1990

[30] Foreign Application Priority Data

May 25, 1989 [DE] Fed. Rep. of Germany ....... 3917046

[51] Int. Cl.$^5$ ............... C09B 62/085; C09B 62/09; C09B 19/00; C07D 251/50
[52] U.S. Cl. ........................ 534/598; 534/618; 534/635; 534/637; 534/638; 540/126; 544/76; 544/208
[58] Field of Search ............ 544/204, 187, 76, 208, 544/209; 534/598, 618, 635, 637, 638; 540/126

[56] References Cited

U.S. PATENT DOCUMENTS

| | | | |
|---|---|---|---|
| 4,189,570 | 2/1980 | Bonometti et al. | 544/211 |
| 4,261,889 | 4/1981 | Seiler et al. | 544/204 X |
| 4,294,580 | 10/1981 | Henk et al. | 544/204 X |
| 4,556,706 | 12/1985 | Hegar et al. | 534/618 |
| 4,614,818 | 9/1986 | Dritz et al. | 544/204 X |
| 4,740,597 | 4/1988 | Frank et al. | 544/204 X |
| 4,906,737 | 3/1990 | Seiler et al. | 544/204 X |

OTHER PUBLICATIONS

Abstract of JP 62-148,473.
Abstract of JP 55-102,574.

*Primary Examiner*—Mary C. Lee
*Assistant Examiner*—Fiona T. Powers
*Attorney, Agent, or Firm*—Sprung Horn Kramer & Woods

[57] ABSTRACT

A new process for the preparation of substituted 2,4-diamino-6-flurotriazines of the formula $$\begin{array}{c} R_1 \\ \diagdown \\ R_2 \end{array} N - \underset{\underset{\underset{F}{\diagdown}}{\overset{N}{\diagup}}}{\overset{N}{\diagdown}} - N \underset{R}{+A+}(SO_3M)_{1-3} \qquad (I)$$

in which the substituents have the meanings given in the description, comprises reacting ammonium salts of the formula $$H-\underset{R}{\overset{}{N}}+A+SO_3^{\ominus}\ (SO_3M')_{0-2}\quad H_2\overset{\oplus}{N}\diagdown\underset{R_2}{\overset{R_1}{\diagup}} \qquad (II)$$

in an aqueous medium at pH values of about 2.5–10 with 2,4,6-trifluorotriazine in a continuous process. The reaction products can be converted to dyestuffs without isolating the intermediates.

5 Claims, No Drawings

PROCESS FOR THE PREPARATION OF SUBSTITUTED 2,4-DIAMINO-6-FLUORO-S-TRIAZINES

The present invention relates to a condensation process for the preparation of substituted 2,4-diamino 6-fluorotriazines of the formula

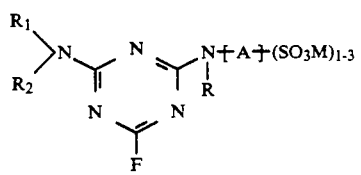
(I)

characterized in that ammonium salts of the formula

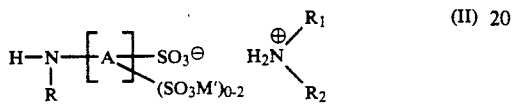
(II)

in which
A is a chromophoric or non-chromophoric aromatic-carbocyclic or aromatic-heterocyclic radical
M is an alkali metal cation
R is H or $C_1$–$C_4$-alkyl
$R_1$, $R_2$, independently of one another, are hydrogen, an aliphatic or cycloaliphatic radical or together with the N atom a 5- or 6-membered heterocyclic radical and
M' is M or H
are reacted continuously with 2,4,6-trifluorotriazine (III) in aqueous media at pH values of about 2.5–10.0, preferably in such a manner that cyanuric fluoride and an aqueous solution of the ammonium salt (II) are simultaneously and continuously passed into a first reactor, vigorously mixed there, and the reaction mixture is then passed into a second reactor in which only slight demixing but good radial mixing takes place, and the primary condensation is completed there. The second fluorine atom is then exchanged in this reactor continuously or in a third reactor continuously or batchwise by metering in bases, for example alkali metal carbonate or alkali metal hydrogen carbonate.

Suitable cations M are in particular $Na^+$, $K^+$, $Li^+$.

Suitable radicals A are in particular those of the benzene or naphthalene series, in particular those which additionally have OH and/or $NH_2$ groups.

The alkyl radicals R can be unsubstituted or substituted, for example, by OH, Cl, COOH, $SO_3H$, $OSO_3H$.

Examples of suitable radicals $R_1$ and $R_2$ are unsubstituted or substituted $C_1$–$C_4$-alkyl (substituents: OH, CN, COOH, $SO_3H$, $OSO_3H$, $OC_1$–$C_4$-alkyl, $N(C_1$–$C_4$-alkyl)$_2$, $C_1$–$C_4$-alkylcarbonylamino, phenyl, sulphophenyl and $SO_2X$ where X is $CH=CH_2$, $CH_2CH_2OSO_3H$, $CH_2CH_2Cl$, $CH_2Ch_2SSO_3H$, $CH_2CH_2OCOCH_3$) or together with the N atom:

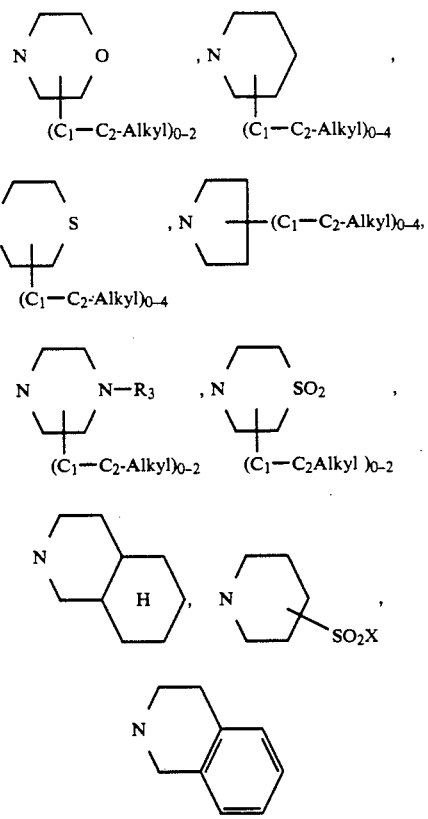

in which X has the abovementioned meaning and $R_3$ is H, substituted or unsubstitued $C_1$–$C_4$ alkyl, (substitutents in particular OH, $OSO_3H$, $SO_2X$).

Indiviudal radicals $R_1$ and $R_2$ are as follows: $Ch_3$, $C_2H_5$, $C_3H_7$, $C_4H_9$, (branched or straight-chain), $CH_2CH_2OH$, $CH_2CH_2CN$, $CH_2CO_2H$, $CH_2CH_2CO_2H$, $CH_2CH_2SO_3H$, $CH_2SO_3H$, $CH_2CH_2OSO_3H$, $CH_2CH_2CH_2OH$, $CH_2CH_2CH_2OSO_3H$, $CH_2$—CH(OH)—$CH_3$, $CH_2CH_2NHCOCH_3$, $CH_2CH_2OCH_3$, $CH_2CH_2OCH_2CH_3$, $CH_2CH_2CH_2OC_2H_5$, $CH_2CH_2N(CH_3)_2$, $CH_2CH_2CH_2N(CH_3)_2$, cyclohexyl, benzyl, sulphobenzyl, $CH_2CH_2$—$C_6H_5$ and

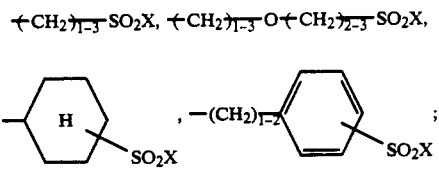

Particularly suitable starting compounds (II) are those of the formula

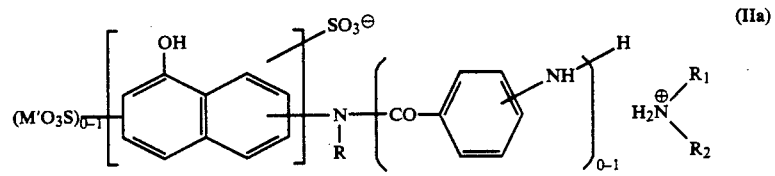
(IIa)

which, when reacted with cyanuric fluoride, give compounds of the formula

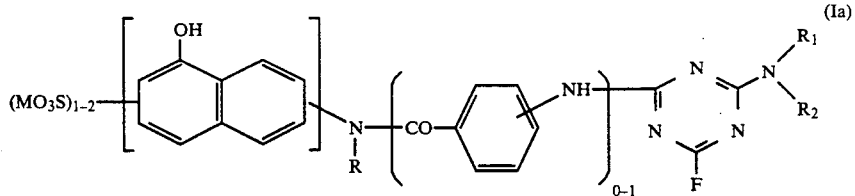

The ammonium salts (II) are obtained in a known manner by adding 1 mol of amine $HNR_1R_2$ (IV) to the aqueous solution of 1 mol of acid

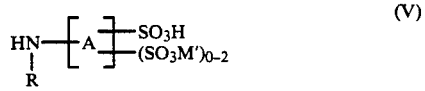

Individual radicals $+A+(SO_3M')_{1-3}$ written in the form of the free acids—are as follows:

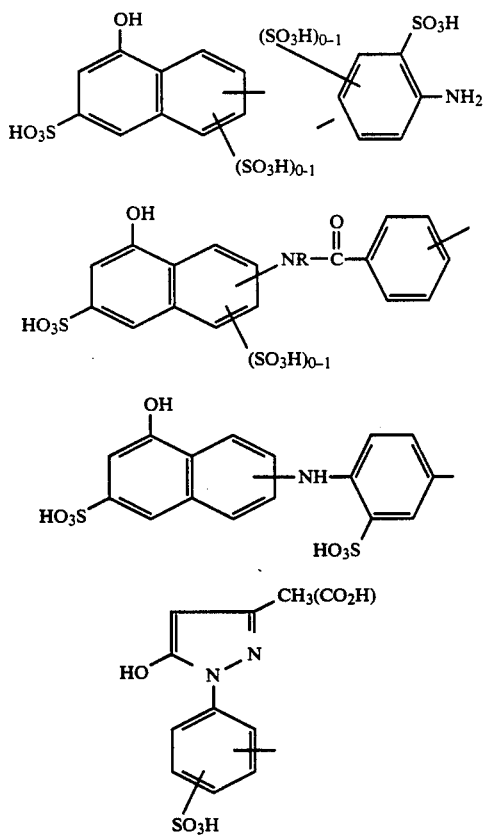

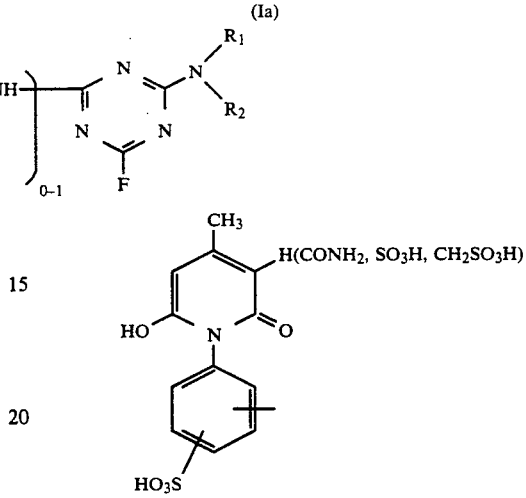

Examples of suitable acids (V) on which the ammonium salts (II) are based are:
8-amino-1-hydroxynaphthalene-3,5-disulphonic acid
8-amino-1-hydroxynaphthalene-3,6-disulphonic acid
7-amino-1-hydroxynaphthalene-3,6-disulphonic acid
6-amino-1-hydroxynaphthalene-3,5-disulphonic acid
6-amino-1-hydroxynaphthalene-3-sulphonic acid
6-methylamino-1-hydroxynaphthalene-3-sulphonic acid
7-amino-1-hydroxynaphthalene-3-sulphonic acid
7-methylamino-1-hydroxynaphthalene-3-sulphonic acid
5-amino-1-hydroxynaphthalene-3-sulphonic acid
8-(4-aminobenzoyl)amino-1-hydroxynaphthalene-3,5-disulphonic acid
8-(2-aminobenzoyl)amino-1-hydroxynaphthalene-3,5-disulphonic acid
8-(4-aminobenzoyl)amino-1-hydroxynaphthalene-3,6-disulphonic acid
8-(2-aminobenzoyl)amino-1-hydroxynaphthalene-3,6-disulphonic acid
8-(3-aminobenzoyl)amino-1-hydroxynaphthalene-3,6-disulphonic acid
7-(4-aminobenzoyl)amino-1-hydroxynaphthalene-3-sulphonic acid
6-(2-aminobenzoyl)amino-1-hydroxynaphthalene-3-sulphonic acid
2,4-diaminobenzenesulphonic acid
2,5-diaminobenzenesulphonic acid
2,5-diaminobenzene-1,3-disulphonic acid
2,5-diaminobenzene-1,4-disulphonic acid
2,4-diaminobenzene-1,5-disulphonic acid
6-(4-amino-2-sulphophenyl)amino-1-hydroxynaphthalene-3-sulphonic acid
7-(4-amino-2-sulphophenyl)amino-1-hydroxynaphthalene-3-sulphonic acid Examples of suitable chromophoric amines (V) on which the ammonium salts (II) are based are:

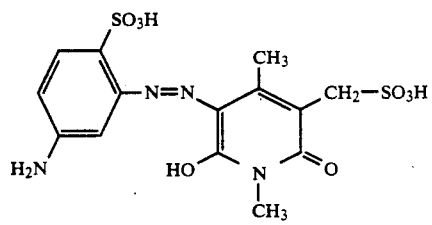
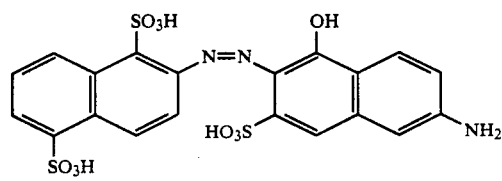
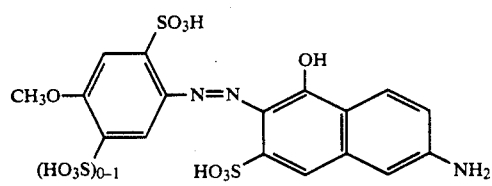
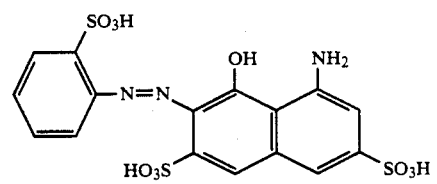
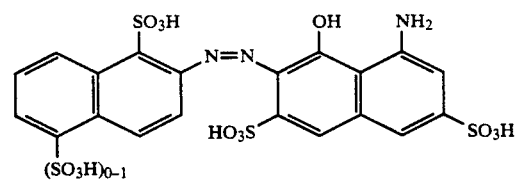
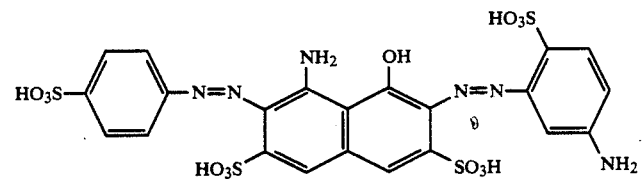
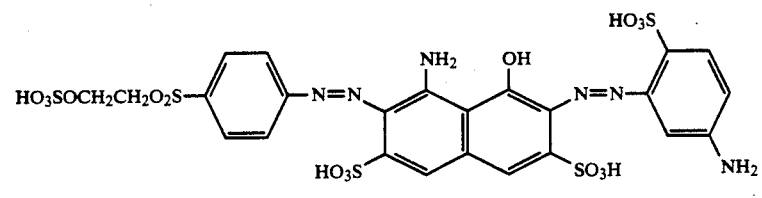

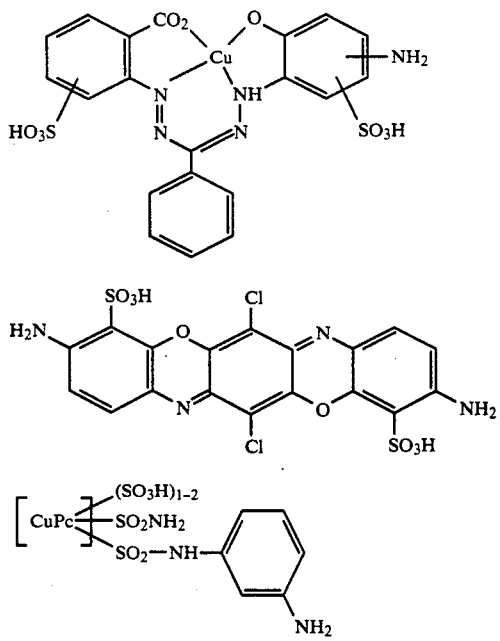

The reaction of (II) with (III) is in general carried out in a molar ratio of 0.8:1 to 1.5:1, preferably 1:1 to 1.2:1, in particular 1:1 to 1.08:1.

The reaction takes place in an aqueous medium, in general in a solution, but it can also be carried out in an aqueous suspension. The reaction temperatures are $-5°$ C. to $+20°$ C., preferably $-2°$ C. to $+10°$ C.

Advantageously, an inert gas atmosphere such as nitrogen or argon is employed.

The reaction is preferably carried out in the presence of sufficient amounts of buffer substances such as alkali metal fluorides, alkali metal borates, alkali metal acetates.

The buffer substances are in general used in an amount of 0.5 to 2, preferably 0.8 to 1.2, moles per mole of amine.

In this reaction, a pH range of about 2.5 to 6 is initially established (exchange of the 1st fluorine atom) and then a pH range of about 6–10 by metering in bases such as alkali metal hydroxides, alkali metal carbonates or alkali metal bicarbonates (Li, Na, K).

The bases are used in amounts of about 0.5 to 1.5 mol per mole of (II).

The detailed procedure of the reaction is as follows:

The educts are simultaneously and continuously passed into a first reactor where vigorous mixing takes place, for example by means of a suitable dispersing unit, such as a rotor/stator mixing head, at approx. 1,000 to 25,000 revolutions per minute or an ultrasound mixing chamber or a static mixing device. The residence time in this first reactor should be as short as possible, but it must be such that sufficient mixing takes place. In general, the residence time in the first reactor is a maximum of 5 seconds, preferably a maximum of 1 second.

During this time, a reaction of the cyanuric fluoride with the ammonium salt of the amine of formula (II) already takes place to some extent. It has proven to be favourable, in particular if the amine used is an aminonaphtholsulphonic acid, if the maximum conversion in the first reactor is 50%, preferably 30%. This is achieved by a small volume of the first reactor or by a short residence time.

The reaction mixture is passed from the first reactor to a second reactor, and the first condensation reaction is completed there. A suitable second reactor is in general any reactor in which only a small amount of demixing but good radial mixing takes place. Preferably, a tubular reactor which has a good plug flow profile and operates in the turbulent flow region is used. Tubular reactors which have a laminar flow can also be used if they are equipped with suitable static mixing elements for improving the radial mixing. This second reactor is, if necessary, cooled to maintain the temperature in the desired range. The residence time of the reaction mixture in the second reactor depends inter alia on the type of amine and the temperature and is in general between about 30 seconds and 5 minutes.

First, the mixture goes through a pH range of about 2.5–6, and is then adjusted to a pH range of 6–10 by metering in bases, such as, for example, alkali metal hydroxide, alkali metal carbonate or alkali metal bicarbonate, until the second halogen atom is completely exchanged.

The increase in the pH is preferably carried out either at the end of the second reactor or, alternatively, in a third reactor. It is, of course, also possible to carry out the pH control in a stirred boiler.

Surprisingly, the reaction takes place at a fast rate, in high yields and leads to very uniform reaction products. Undesired symmetrical biscondensation products are formed, if at all, in traces.

The disadvantages of the known two-step processes (cf. DE-A (German Published specification) 2,741,011, 2,903,594, 3,545,460; non-uniform reaction products, hydrolysis products) are not formed in this process.

The resulting reaction products or reactive dyestuffs of the formula (I) can be isolated, although in the case where A is a non-chromophoric radical they are preferably processed to give reactive dyestuffs without isolating the intermediate.

This further processing—coupling or diazotization reaction of (I)—can be carried out batchwise or continuously in a known manner.

The invention accordingly also relates to a process for the preparation of reactive dyestuffs in which compounds of the formula (I) where A is a radical of a coupling component or a radical of a diazo component are first prepared according to claim 1 and then, without isolating the intermediates, continuously or batchwise coupled onto diazotized amines in a conventional manner or diazotized and, without isolating the intermediates, coupled continuously or batchwise onto coupling components.

EXAMPLE 1

In a first reactor (dispersing unit), 8.8 ml of trifluoros-triazine which has a temperature of 20°–25° C. and 200 ml of an aqueous solution at 0° C., prepared by the addition of 34.1 g of the monosodium salt of 1-hydroxy-8-aminonaphthalene-3,6-disulphonic acid, 9.0 g of morpholine, 5 g of sodium fluoride and 40 g of ice in 140 ml of water, are simultaneously and continuously fed in via separate inlet lines.

In the reactor, an even, rapid mixing of the phases is achieved with the aid of a dispersing device during a residence time of 0.2–1.0 second in combination with high turbulence. The reaction mixture is passed from the first reactor through a cooled tubular reactor which has a good plug flow profile. The residence time in the tubular reactor is about 15–30 seconds.

The reaction mixture leaves the reactor at a temperature of about 3° C. and a pH of about 4.2. The resulting reaction mixture is passed into a stirred boiler and adjusted there to a pH of 7.0 within 10 minutes by dropwise addition of a sodium carbonate solution and maintained at this value. This is followed by slow crystallization of the condensation product of the formula

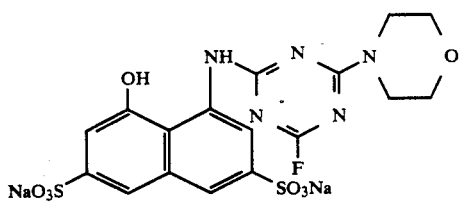

which can be isolated by filtering it off with suction. However, since the condensation reactions lead to a uniform product, the reaction mixture can also directly be reacted further; thus, for example, it can be coupled onto diazotized 2-aminonaphthalene-1-sulphonic acid to give a valuable red monofluoride triazine reactive dyestuff.

The procedure is repeated as described, except that the morpholine in Example 1 is replaced by an equivalent amount of another amine, for example dimethylamine, diethylamine, piperidine, methylamine, benzylamine or 2-methylaminoethanol, also to give the correspondingly substituted uniform dicondensation products of the formula

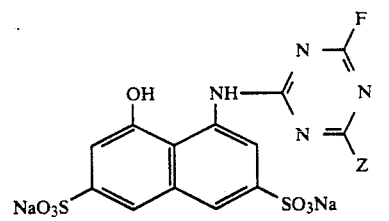

a) Z = N(CH₃)₂   d) Z = NHCH₃ b) Z = N(C₂H₅)₂   e) Z = NHCH₂—⌬

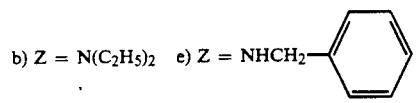

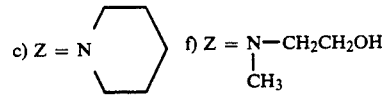

EXAMPLE 2

23.9 g of 1-hydroxy-6-aminonaphthalene-3-sulphonic acid are stirred in 200 ml of water and dissolved by the addiion of 6.3 g of 2-aminoethanol. 5 g of sodium fluoride and 50 g of ice are added to this solution, which is then brought to a pH of 6.0 with dilute hydrochloric acid. The solution is simultaneously and continuously fed into the first reactor together with 8.8 ml of trifluorotriazine via separate inlet lines. The reaction is continued as described in Example 1 to give, after the addition of sodium carbonate, a reaction mixture of the dicondensation product of the formula

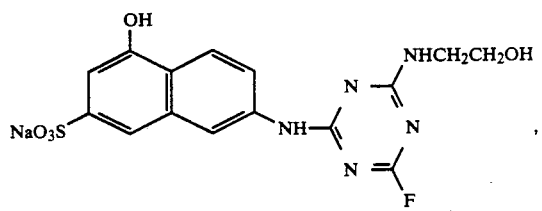

which can be reacted, without isolating the intermediate, with diazotized anilines to give interesting azo reactive dyestuffs.

EXAMPLE 3

The procedure according to Example 1 is repeated, except that 18.8 g of 2,4-diaminobenzenesulphonic acid are used instead of the monosodium salt of 1-hydroxy-8-aminonaphthalene-3,6-disulphonic acid, to give a relatively uniform dicondensation product of the formula

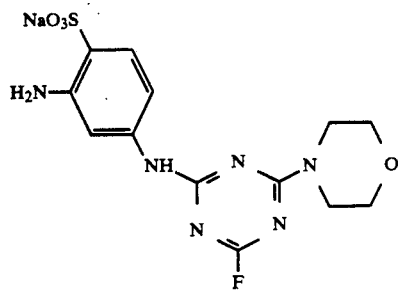

which can be converted into a valuable diazonium salt component by diazotization at 0° C. and a pH of 2.0 to 2.5.

EXAMPLE 4

The condensations according to Example 1 are repeated, except that 59.5 g of the dyestuff base of the formula

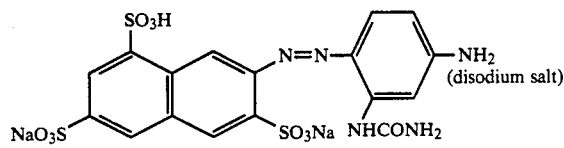

is now used instead of the colourless 1-hydroxy-8-amino-naphthalene-3,6-disulponic acid (monosodium salt) of Example 1, to give a reactive dyestuff of the formula

which is isolated by salting it out and dyes cotton in clear golden yellow shades, which have excellent fastness properties.

We claim:

1. A process for the preparation of a substituted 2,4-diamino-6-fluorotriazine of the formula

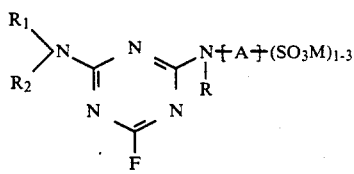

comprising continuously reacting an ammonium salt of the formula

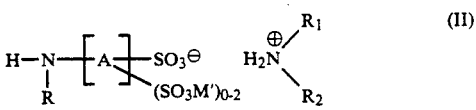

in which

A is a chromophoric or non-chromophoric aromatic-carboxylic or aromatic-heterocyclic radical, M is an alkali metal, R is H or $C_1$-$C_4$-alkyl, $R_1$, $R_2$ independently of one another, are hydrogen, an aliphatic or cycloaliphatic radical or together with the N atom a 5- or 6-membered heterocyclic radical, and M' is M or H, with 2,4,6-trifluorotriazine (III) in the absence of a strong base at a pH of about 2.5-6, then adding a strong base and completing the reaction at a pH of about 6-10.

2. A process accoridng to claim 1, wherein the molar ratio of (II):(III) is 0.8:1-1.5:1.

3. A process according to claim 1, wherein the condensation reaction is carried out in the presence of a buffer.

4. A process according to claim 3, wherein the condensation is carried out in the presence of NaF as the buffer, and the strong base added to complete the reaction is an alkali.

5. A process according to claim 3, wherein about 0.5 to 2 moles of the buffer is present per mole of (II).

* * * * *